Figure 1:
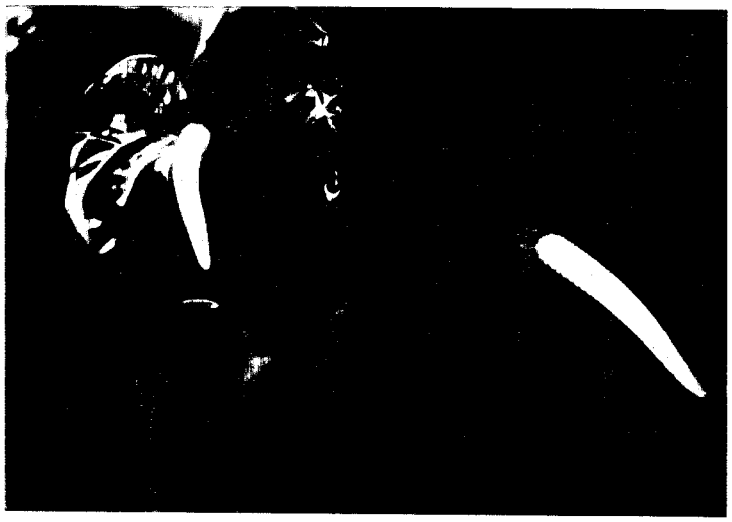

United States Patent [19]

Rotolante

[11] Patent Number: Plant 7,760

[45] Date of Patent: Dec. 31, 1991

[54] ANTHURIUM 'ROTOLANTE #1'

[75] Inventor: Denis W. Rotolante, Homestead, Fla.

[73] Assignee: Oglesby Plant Laboratories Inc., Altha, Fla.

[21] Appl. No.: 586,140

[22] Filed: Sep. 21, 1990

[51] Int. Cl.[5] ..... A01H 5/00

[52] U.S. Cl. ..... Plt./88

[58] Field of Search ..... Plt./88

*Primary Examiner*—James R. Feyrer

*Attorney, Agent, or Firm*—Frank B. Robb

[57] ABSTRACT

An Anthurium cultivar of fast growth, loose somewhat spreading habit, many branches, displaying freely blooming characteristics and extreme change in color of blooms from initial development to maturity, being dark purple nearly black to ultimately a bright red, appearing to be almost a different plant by those changes.

1 Drawing Sheet

GENERAL DESCRIPTION OF THE INVENTION

There is disclosed a new Anthurium plant of the *Anthurium andreanum* species.

I discovered my new Anthurium plant among a group of Anthurium known as 'Obaki' which plant is unpatented.

I have satisfied myself that the plant is the result of natural pollination from an unknown source which occurred in a cultivated area of the nursery which I operate in the vicinity of Homestead, Fla.

In the nursery, we produce substantial quantities of Anthurium and I have also crossed certain varieties in an effort to produce new cultivars of varying forms, colors and characteristics.

I have caused my new plant to be asexually reproduced by tissue culture, and find that it comes true in successive generations which have been produced over time.

As will be understood from a consideration of the drawing, my new plant has some outstanding differences from known varieties, in particular the changing of color of the flower as it matures.

The disclosure in the drawing is as nearly representative of the extremes in color which occur during the maturing process, as where FIG. 1, shows the initial coloration at the beginning stages when the flower is fully opened, wherein the color may be described as a deep purple, very dark and unusual.

Figure 2:
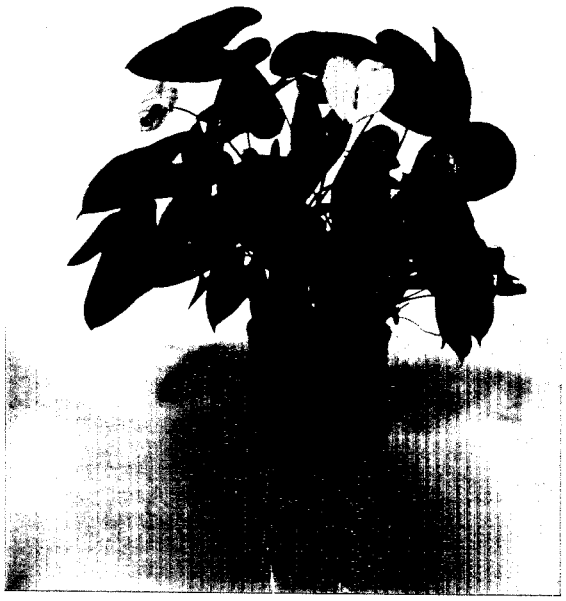

As the flower matures, it changes color and in FIG. 2 a complete plant shows flowers with the very much brighter red color which prevails at maturity.

Thus I have disclosed a unique characteristic of rather radical change in color from the first stages of bloom until the aging of the bloom, which presents a very different appearance from other Anthurium varieties or cultivars with which I am familar.

Other characteristics of the plant as to color of stem and petioles are affected by changes in lighting intensity such that in higher light, red pigmentation appears, unevenly dispersed therealong.

It may be helpful to make some general comparison with Anthurium plants grown under similar conditions in the vicinity of Altha, Fla. where the characteristics of plants of my development have been consistent.

Anthurium 'Rosa' an unpatented variety exhibits a more compact growth habit, with pink (48D) flowers as contrasted with my plants which I have chosen to designate as Rotolante #1 for commercial use.

Anthurium 'Ozaki Red' (unpatented) with a flower color of light red (47-A-B), displays less lateral branching than 'Rotolante #1' and the plant, Oglesby's 'Lady Jane' Anthurium (unpatented) is of more compact growth habit with smooth, narrower flowers (pink 51B) than my plant and leaves of darker green (139A).

Detailed characteristics of my plant are set forth hereinafter and where color is referred to as before and hereafter, The Royal Horticultural Society Colour Chart is used as a basis for comparing with the illustrations made by photographic process which is as nearly true as possible to make by such means.

It is particularly difficult to obtain illustrations of the darker colors displayed, but those shown are as nearly true as can be supplied.

Parentage:

*Seed parent.*—*Anthurium andreanum* 'Obaki' (Unpatented).

*Pollen parent.*—Unknown natural pollination that occurred at greenhouse facility.

Propagation: Plant tissue culture in vicinity of Altha, Fla.

Classification: *Anthurium andreanum* hybrid.

Plant descriptions:

*Stem.*—Smooth. Stem color between newest leaf and next oldest leaf has green (144 B) background with accumulation of red (approx 53 D) pigmentation unevenly dispersed. The red pigmentation is most obvious under higher lighted growing conditions or where the stem is exposed to direct light. Stem color below second leaf approximates green 144 A-B.

*Lenticels.*—Not obvious.

*Petioles.*—30–40 cm. Smooth. Color when young — green (144 B). As petioles age an accumulation of red pigmentation occurs unevenly distributed along the length of the petiole. The red color approximates (52 A). As with the stems, the pigmentation is most evident on petioles exposed to direct light.

*Leaves.*—20–30 cm. long by 12–14 cm. wide depending on age. Ovate, Sagittate base, Acuminate tip. Basal lobes extend 5–8 cm. above point of petiole attachment to leaf blade. Entire margins Reflexed. Color — New leaf 144 A adaxial.

Polished 146 D abaxial. Old leaf 137B adaxial. Dull 146 B-C abaxial. Texture — Leathery, smooth. Veins — Main vein (Rib) prominent near base of leaf. Both main rib and lateral veins near base of leaf protrude from leaf surface. Veins in remainder of leaf are even with leaf surface to somewhat sunken. Main rib and major lateral veins near base of new leaf have reddish tint (approx. 52 A) fading as leaf ages to green (150 B-C).

*Leaf sheath.*—Surrounds young leaf during early developmental stages and is directly attached to the stem below the leaf attachment. The leaf surrounding the newest leaf is green (144 B) with reddish pigment accumulation approximating (52 A). With age the sheath color changes to green (144 B) without any pigmentation and eventually turning light brown (165 B-C) and finally dark brown (165 A-B). The sheath is 8–12 cm. long and 1–2.5 cm. wide where sheath attaches to stem.

*Flowers.*—Type: Spathe and Spadix. Spathe tightly rolled around Spadix during development. The spathe is fully opened when peduncle is fully elongated. Shape: Rounded heart shape (orbicular-ovate). Spathe: Spreading. Puckered. Polished. 8–13 cm. wide×8–13 cm. long. Size of flower is dependent on age of plant Base — cordate-sagittate; sinus formed at juncture of lobes. Tip — cuspidate. The extreme end of the tip is green (145 B-C). Color — Fully expanded. Adaxial, Red (187 A). (Color of the abaxial (back) side typically becomes lighter towards the margins. The change in color is most pronounced towards the basal lobes of the spathe. The center of the abaxial side approximates red (187 A) and fades to (187 C) towards the margins. Veins — obvious, protrude above spathe adaxial surface.

*Peduncle.*—37–49 cm. long. Color when young green (144 A-B). As the peduncle ages it accumulates red pigmentation which approximates the color (46 A). Generally the peduncle displays more red pigment then the petioles or stem.

Reproductive organs:

*Spadix.*—6–8 cm. long. 16–22 mm. dia. at base 9.5–13 cm. dia. 5 mm. below tip. Color — Spadix-tip white blending to yellow (15C) in the middle blending to light green (151 D) near the base. As the spadix continues to age the white tip eventually turns yellow (15 C) then changing to green.

*Stamens.*—Anthers and filaments not clearly visible.

*Pistils.*—Sitting between stamens, firmly fixed to main axil.

Flowering time: After approximately 9–12 months depending on season 1–4 blossoms will be present. Smaller flowers may occur on less mature plants.

Roots: Root developed above soil line are fleshy light brown-green in color and non-branching. Roots developed below the soil line are fleshy and well branched with fine lateral roots.

Diseases: Initial greenhouse trials in Homestead, Fla. and Altha, Fla. indicate good resistance against traditional diseases.

*Insects.*—No unusual susceptibility to insects noted to date.

GENERAL OBSERVATIONS

Anthurium Rotolante #1 is a fast growing Anthurium with a loose or slightly spreading growth habit. This new cultivar produces numerous branches which with maturity flower freely. Its freely branching and flowering characteristics make this new cultivar well suited as a pot plant or cut flower.

I claim:

1. A new and distinct Anthurium cultivar substantially as herein shown and described, characterized particularly as to novelty by its fast growth with a loose, slightly spreading growth habit, numerous branches which flower freely upon maturity, its range of flower color from initial period when very dark, blood red color of flower, changes as the flower matures by noticeable stages to a rather bright red color at maturity.

* * * * *